E. SCHOFIELD.

Combined Inhaler and Nasal-Douche.

No. 6,260. Reissued Jan. 26, 1875.

Witnesses.

Chas. H. Burleigh

Percy Mott

Inventor.

Edwin Schofield

THE GRAPHIC CO. PHOTO-LITH. 39 & 41 PARK PLACE, N.Y.

UNITED STATES PATENT OFFICE.

EDWIN SCHOFIELD, OF WORCESTER, MASSACHUSETTS.

IMPROVEMENT IN COMBINED INHALERS AND NASAL DOUCHES.

Specification forming part of Letters Patent No. 135,372, dated January 28, 1873; reissue No. 6,260, dated January 26, 1875; application filed December 27, 1873.

*To all whom it may concern:*

Be it known that I, EDWIN SCHOFIELD, of the city and county of Worcester and Commonwealth of Massachusetts, have invented certain new and useful Improvements in Inhaling Apparatus and Nasal Douche; and I hereby declare that the following is a full, clear, and exact description of the same, reference being had to the accompanying drawings, which form a part of this specification, and in which—

Figure 1:
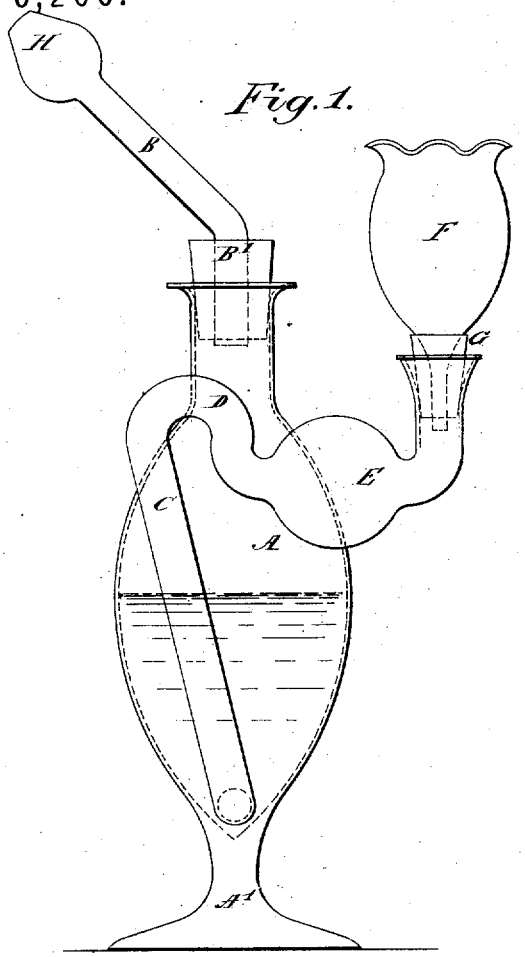
Figure 3:
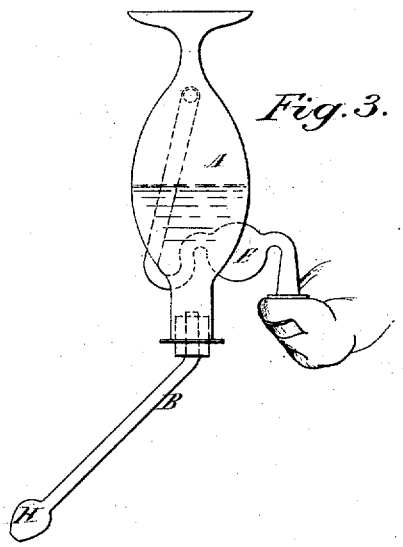
Figure 2:
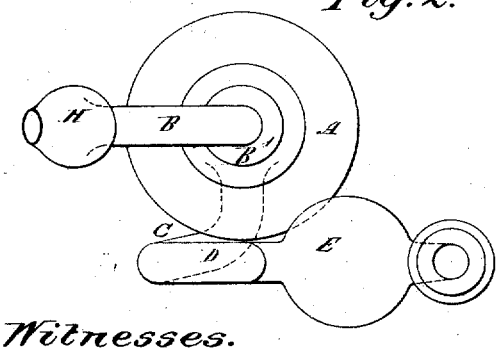

Figure 1 represents a side view of an inhaler and nasal-douche apparatus embracing my improvements. Fig. 2 represents a plan view, and Fig. 3 represents the apparatus as used for a nasal douche.

The object of my invention is to provide a simple and convenient apparatus for facilitating the application of medicated vapors, fumes, or baths to the membranes or tissues affected in cases of catarrh, bronchitis, and similar diseases; and to this end my invention consists, first, in the employment, in an inhaling apparatus, of a main receptacle or reservoir, for containing ammoniated liquid, provided with a draft or exhaust tube, and having a single inlet-passage for air, terminating in the lower part of said receptacle, and provided with an acidifier, communicating with said passage at a position between the exterior inlet-orifice and the opening of the passage to the interior of the main receptacle, the parts being arranged for operation so that all air passing through the apparatus will be first subjected to the fumes from the acid contained in the acidifier, and thereafter delivered in contact with or through the ammoniated liquid in the main receptacle, thus insuring proper chemical union of the acid and alkaline elements, and the generation of an inhalent vapor of uniform quality; second, in an acidifier having a continuous inlet and outlet passage above the surface-level of an acid liquid contained therein, in combination with the inlet-passage of an inhaling apparatus, for the purpose set forth; third, in the peculiar inlet-tube, in combination with the main receptacle and draft-tube of an inhaling apparatus, substantially as set forth.

In the drawings, the part marked A indicates the main receptacle, which, in the present instance, is of oval form, and is provided with a foot or stand, A′, and has a neck and opening at its upper part to receive the stopper or packing B′, in which the end of the draft-tube B is held, said tube being passed through the stopper or packing so as to communicate with the interior upper part of the receptacle A. C indicates the inlet-tube, the air-passage through which communicates with the interior of the main receptacle or vessel A at its lower part, while the upper portion of the tube C is bent or turned so as to form a dip or siphon curve, D, in the passage, and an acidifier chamber or bulb, E, is formed therein at a position above the level of the liquid in the main receptacle A, and between the bend D and inlet-orifice of the air-passage. The end of the tube, in the present instance, is turned upward, so that the inlet-orifice is somewhat higher than the bulb E, and its end is expanded in bell or funnel shape, so that a pipe-bowl or tobacco-receptacle, F, may be used with the tube when desired, the parts to be fitted and made tight to each other by a suitable stopper or packing, G, as indicated in Fig. 1 of the drawings.

The bulb E, or acidifier-chamber, is for holding the supply of hydrochloric acid, or other medicinal acid liquid, used in the production of the vapor or gas to be inhaled, while the ammoniated liquid or alkaline element I place within the main receptacle or vessel A, the proportional quantities of each being indicated in the drawing by the horizontal lines. The air passes through the inhaler, when in use, in a single current, entering through the tube C, and passing out to the patient through the tube B, the inhalent vapor being generated within the receptacle A as the air passes through. The inlet-passage is so formed that the point of entrance for air into the acidifier and its point of exit therefrom are above the level of the liquid acid contained therein, the air-passage being continuous with the acidifier. By a continuous passage is meant one unbroken by the passage of the air through the body of the acid itself, the acidifier-space being a portion of, or undivided from the other portions of, the air-inlet channel.

The incoming air is thus caused to flow in contact with the surface of the acid, and to become impregnated with the light fumes or vapors that rise therefrom, and while thus charged with acid the air is delivered, by the tube C, into the ammoniated liquid in the receptacle A at its lower part, causing the acid vapor borne by the air to be brought into contact with the ammonia contained in the liquid as the air-bubbles rise from the end of the tube C to the surface of the liquid, and the inhalent gas or chloride of ammonia is thus generated, which gas then passes to the patient through the tube B.

One important feature of my invention is, the arrangement of parts as set forth, whereby the entire air first becomes acidified and then ammoniated while passing from the inlet-orifice to the draft-tube. This insures the neutralization or proper chemical union of the acid and alkaline elements, and the generation of an inhalent gas of uniform quality, and obviates the liability of receiving an excess of either acid or alkali—a result sometimes occurring where there are separate air-inlets for the acidifier and ammoniator.

To use the apparatus as a nasal douche the vessel A is to be filled with water, which may be medicated or otherwise, as desired. The thumb is then placed over the end of the inlet-tube C, and the apparatus inverted, as shown in Fig. 3. By placing the end of tube B to one nostril, and removing the thumb from the end of the tube C, air is admitted into the receptacle A above the liquid, which latter is thus permitted to flow through the passage of the nose. By means of the thumb upon the end of the tube C the patient is enabled to regulate the flow of the liquid at pleasure.

Separate tubes B may be used for the nasal-douche and inhaling processes, one being formed plain, and the other being provided with a bulbed end, H, the tubes being interchangeable in the stopper B′.

The main receptacle A, draft-tube B, inlet-tube C, and pipe-bowl F are, in the present instance, all made from glass; but, if preferred, other suitable materials may be used, as meerschaum for the pipe-bowl F, and rubber or other flexible tubing for the draft-tube B. The main vessel A, inlet-tube C, and acidifier E are, however, preferably of clear glass.

It will be understood that the pipe-bowl F is not employed when using the apparatus for inhaling, said bowl being for the convenience of those desiring smoke fumes.

Having described my improvements in inhaling apparatus, what I claim therein as my invention, and desire to secure by Letters Patent, is—

1. The combination, in an inhaling apparatus, of a main reservoir for containing ammoniated liquid, provided with a draft-tube, a single inlet-passage, and an acidifier, when said parts are arranged for operation so that all air passing through the apparatus first becomes impregnated with acid fumes, and is thereafter delivered in contact with or through the ammoniated liquid contained in said main reservoir, for the purpose set forth.

2. An acidifier having a continuous inlet and outlet passage above the surface-level of an acid contained therein, in combination with the inlet-passage of an inhaling apparatus, for the purpose set forth.

3. In combination with the main receptacle of an inhaling apparatus, an inlet-tube constructed with a bend, D, and bulb E between said bend and the mouth of the tube, substantially as set forth.

4. The inhaling and nasal-douche apparatus, consisting of the receptacle A, bulbed inlet-tube C E, and draft-tube B, furnished with the nasal plug H, as herein shown, and for the purpose set forth.

EDWIN SCHOFIELD.

Witnesses:
CHAS. H. BURLEIGH,
PRESBURY WEST.